(12) United States Patent
Addison et al.

(10) Patent No.: US 9,155,493 B2
(45) Date of Patent: Oct. 13, 2015

(54) METHODS AND APPARATUS FOR CALIBRATING RESPIRATORY EFFORT FROM PHOTOPLETHYSMOGRAPH SIGNALS

(75) Inventors: Paul Stanley Addison, Edinburgh (GB); James N. Watson, Dunfermline (GB)

(73) Assignee: Nellcor Puritan Bennett Ireland, Mervue (IE)

( * ) Notice: Subject to any disclaimer, the term of this patent is extended or adjusted under 35 U.S.C. 154(b) by 1139 days.

(21) Appl. No.: 12/771,792

(22) Filed: Apr. 30, 2010

(65) Prior Publication Data

US 2011/0270114 A1  Nov. 3, 2011

(51) Int. Cl.
  A61B 5/08  (2006.01)
  A61B 5/087  (2006.01)
  A61B 5/00  (2006.01)
  A61B 5/1455  (2006.01)

(52) U.S. Cl.
  CPC . *A61B 5/08* (2013.01); *A61B 5/087* (2013.01); *A61B 5/4818* (2013.01); *A61B 5/726* (2013.01); *A61B 5/0816* (2013.01); *A61B 5/14551* (2013.01); *A61B 2560/0223* (2013.01)

(58) Field of Classification Search
  CPC .................................. A61B 5/08; A61B 5/087
  USPC ......... 600/484, 529, 533, 538, 532, 535, 537, 600/540, 543
  See application file for complete search history.

(56) References Cited

U.S. PATENT DOCUMENTS

| | | | |
|---|---|---|---|
| 3,532,087 A | 10/1970 | Horn | |
| 3,884,219 A | 5/1975 | Richardson et al. | |
| 3,926,177 A | 12/1975 | Hardway et al. | |
| 4,289,141 A | 9/1981 | Cormier | |
| 4,696,307 A | 9/1987 | Montgieux | |
| 5,143,078 A | 9/1992 | Mather | |
| 5,273,036 A | 12/1993 | Kronberg | |
| 5,439,483 A | 8/1995 | Duong-Van | |

(Continued)

FOREIGN PATENT DOCUMENTS

| | | |
|---|---|---|
| EP | 2017586 | 1/2009 |
| JP | 9-84776 | 3/1997 |

(Continued)

OTHER PUBLICATIONS

International Search Report dated Aug. 24, 2011, Application No. PCT/IB2011/000906 (5 pgs.).

(Continued)

*Primary Examiner* — Jacqueline Cheng
*Assistant Examiner* — Puya Agahi
(74) *Attorney, Agent, or Firm* — Shvarts & Leiz LLP

(57) ABSTRACT

Breathing effort of a patient, as determined (for example) from a photoplethysmograph ("PPG") signal from the patient, can be calibrated in relation to air pressure in the patient's respiratory system. This calibration can be done by subjecting the patient to varying amounts of breathing resistance; and for each such amount, concurrently measuring (1) air pressure in the respiratory system (e.g., in the oral/nasal cavity) and (2) breathing effort (from the PPG signal). Use can be made of this calibration, e.g., during a sleep study of the patient. During such a study, breathing effort, again determined from the PPG signal and occurring, for example, during an apneic event of the patient, can be used to infer air pressure in the respiratory system by using the above calibration.

7 Claims, 15 Drawing Sheets

(56) References Cited

U.S. PATENT DOCUMENTS

| | | | |
|---|---|---|---|
| 5,575,284 A | 11/1996 | Athan | |
| 5,590,650 A | 1/1997 | Genova | |
| 5,632,272 A | 5/1997 | Diab et al. | |
| 5,680,871 A | 10/1997 | Ganshorn | |
| 5,682,898 A | 11/1997 | Aung | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,954,050 A | 9/1999 | Christopher | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,142,953 A | 11/2000 | Burton | |
| 6,171,257 B1 | 1/2001 | Weil et al. | |
| 6,171,258 B1 | 1/2001 | Karakasoglu et al. | |
| 6,208,951 B1 | 3/2001 | Kumar et al. | |
| 6,293,915 B1 | 9/2001 | Amano et al. | |
| 6,325,761 B1 | 12/2001 | Jay | |
| 6,361,501 B1 | 3/2002 | Amano et al. | |
| 6,393,311 B1 | 5/2002 | Edgar, Jr. et al. | |
| 6,398,727 B1 | 6/2002 | Bui et al. | |
| 6,561,986 B2 | 5/2003 | Baura | |
| 6,608,934 B2 | 8/2003 | Scheirer | |
| 6,635,021 B1 | 10/2003 | Sullivan et al. | |
| 6,654,623 B1 | 11/2003 | Kastle | |
| 6,702,752 B2 | 3/2004 | Dekker | |
| 6,709,402 B2 | 3/2004 | Dekker | |
| 6,801,798 B2 | 10/2004 | Geddes et al. | |
| 6,810,277 B2 | 10/2004 | Edgar, Jr. et al. | |
| 6,811,538 B2 | 11/2004 | Westbrook et al. | |
| 6,896,661 B2 | 5/2005 | Dekker | |
| 6,918,878 B2 | 7/2005 | Brodnick | |
| 6,930,608 B2 | 8/2005 | Grajales et al. | |
| 6,931,269 B2 | 8/2005 | Terry | |
| 6,990,426 B2 | 1/2006 | Yoon et al. | |
| 7,001,337 B2 | 2/2006 | Dekker | |
| 7,004,908 B2 | 2/2006 | Sullivan et al. | |
| 7,020,507 B2 | 3/2006 | Scharf | |
| 7,024,235 B2 | 4/2006 | Melker et al. | |
| 7,035,679 B2 | 4/2006 | Addison | |
| 7,043,293 B1 | 5/2006 | Baura | |
| 7,052,469 B2 | 5/2006 | Minamiura et al. | |
| 7,054,453 B2 | 5/2006 | Causevic | |
| 7,054,454 B2 | 5/2006 | Causevic et al. | |
| 7,079,888 B2 | 7/2006 | Oung | |
| 7,127,278 B2 | 10/2006 | Melker et al. | |
| 7,141,021 B2 | 11/2006 | Sullivan et al. | |
| 7,171,251 B2 | 1/2007 | Sarussi | |
| 7,171,269 B1 | 1/2007 | Addison | |
| 7,173,525 B2 | 2/2007 | Albert | |
| 7,203,267 B2 | 4/2007 | De Man et al. | |
| 7,204,250 B1 | 4/2007 | Burton | |
| 7,225,013 B2 | 5/2007 | Geva et al. | |
| 7,246,618 B2 | 7/2007 | Habashi | |
| 7,254,500 B2 | 8/2007 | Makeig | |
| 7,289,835 B2 | 10/2007 | Mansfield | |
| 7,344,497 B2 | 3/2008 | Kline | |
| 7,381,185 B2 | 6/2008 | Zhirnov et al. | |
| 7,398,115 B2 | 7/2008 | Lynn | |
| 7,421,296 B1 | 9/2008 | Benser | |
| 7,515,949 B2 | 4/2009 | Norris | |
| 7,519,488 B2 | 4/2009 | Fu | |
| 7,523,011 B2 | 4/2009 | Akiyama et al. | |
| 7,785,262 B2 | 8/2010 | Melker et al. | |
| 2002/0120207 A1* | 8/2002 | Hoffman | 600/538 |
| 2003/0163057 A1 | 8/2003 | Flick et al. | |
| 2004/0163648 A1 | 8/2004 | Burton | |
| 2005/0022606 A1 | 2/2005 | Partin et al. | |
| 2005/0043616 A1 | 2/2005 | Chinchoy | |
| 2005/0109339 A1 | 5/2005 | Stahmann et al. | |
| 2005/0109340 A1 | 5/2005 | Tehrani | |
| 2005/0188991 A1 | 9/2005 | Sun et al. | |
| 2005/0215915 A1 | 9/2005 | Noda et al. | |
| 2005/0222502 A1 | 10/2005 | Cooper | |
| 2005/0251056 A1 | 11/2005 | Gribkov et al. | |
| 2006/0074333 A1 | 4/2006 | Huiku | |
| 2006/0155206 A1 | 7/2006 | Lynn | |
| 2006/0162728 A1* | 7/2006 | Delache et al. | 128/204.22 |
| 2006/0209631 A1 | 9/2006 | Melese et al. | |
| 2006/0211930 A1 | 9/2006 | Scharf et al. | |
| 2006/0217603 A1 | 9/2006 | Nagai et al. | |
| 2006/0229519 A1 | 10/2006 | Fujiwara et al. | |
| 2006/0241506 A1* | 10/2006 | Melker et al. | 600/529 |
| 2006/0258921 A1 | 11/2006 | Addison et al. | |
| 2006/0265022 A1 | 11/2006 | John et al. | |
| 2006/0270941 A1* | 11/2006 | Xie et al. | 600/529 |
| 2006/0282001 A1 | 12/2006 | Noel et al. | |
| 2007/0016093 A1* | 1/2007 | Rapoport et al. | 600/533 |
| 2007/0021673 A1 | 1/2007 | Arbel et al. | |
| 2007/0073120 A1 | 3/2007 | Li et al. | |
| 2007/0073124 A1 | 3/2007 | Li et al. | |
| 2007/0129647 A1 | 6/2007 | Lynn | |
| 2007/0142741 A1* | 6/2007 | Berthon-Jones et al. | 600/534 |
| 2007/0149883 A1 | 6/2007 | Yesha | |
| 2007/0167694 A1 | 7/2007 | Causevic et al. | |
| 2007/0167851 A1 | 7/2007 | Vitali et al. | |
| 2007/0185406 A1* | 8/2007 | Goldman | 600/533 |
| 2007/0282212 A1 | 12/2007 | Sierra et al. | |
| 2008/0000477 A1 | 1/2008 | Huster et al. | |
| 2008/0045832 A1 | 2/2008 | McGrath | |
| 2008/0060138 A1 | 3/2008 | Price et al. | |
| 2008/0066753 A1* | 3/2008 | Martin et al. | 128/204.23 |
| 2008/0076992 A1 | 3/2008 | Hete et al. | |
| 2008/0082018 A1 | 4/2008 | Sackner et al. | |
| 2008/0171946 A1 | 7/2008 | Hansmann | |
| 2008/0190430 A1 | 8/2008 | Melker et al. | |
| 2008/0202525 A1 | 8/2008 | Mitton et al. | |
| 2008/0214903 A1 | 9/2008 | Orbach | |
| 2008/0243021 A1 | 10/2008 | Causevic et al. | |
| 2009/0221926 A1* | 9/2009 | Younes | 600/529 |
| 2009/0272382 A1* | 11/2009 | Euliano et al. | 128/204.23 |
| 2009/0306528 A1* | 12/2009 | Curti et al. | 600/537 |
| 2009/0326402 A1* | 12/2009 | Addison et al. | 600/529 |
| 2010/0298730 A1* | 11/2010 | Tarassenko et al. | 600/529 |
| 2010/0331716 A1* | 12/2010 | Watson et al. | 600/538 |

FOREIGN PATENT DOCUMENTS

| | | |
|---|---|---|
| WO | WO 00/21438 | 4/2000 |
| WO | WO 01/25802 | 4/2001 |
| WO | WO 01/62152 | 8/2001 |
| WO | WO 01/76471 | 10/2001 |
| WO | WO 03/000125 | 1/2003 |
| WO | WO 03-022149 | 3/2003 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |
| WO | WO 2007-147069 | 12/2007 |
| WO | WO 2008/043864 | 4/2008 |

OTHER PUBLICATIONS

Addison, Paul S., The Illustrated Wavelet Transform Handbook, Taylor & Francis Group, New York, N.Y., 2002.

Addison, Paul, "The Little Wave with the Big Future," Physics World, Mar. 2004, pp. 35-39.

Clifton, D., et al., "Measurement of Respiratory Rate from the Photoplethysmogram in Chest Clinic Patients," Journal of Clinical Monitoring and Computing, 2006.

Legarreta, I. Romero, et al., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2005, pp. 1-24.

(56) References Cited

OTHER PUBLICATIONS

Leonard, Paul A., et al., "A Fully Automated Algorithm for the Determination of Respiratory Rate From the Photoplethysmogram," Journal of Clinical Monitoring and Computing, vol. 20, No. 1, 2006, pp. 33-36.

Leonard, Paul A., et al., "An Automated Algorithm for Determining Respiratory Rate by Photoplethysmogram in Children," Acta Paediatrica, vol. 95, 2006, pp. 1124-1128.

Yamada, Michio, "Wavelet Analysis and Its Application," Journal of the Institute of Electronics, Information and Communication Engineers, vol. 76, No. 5, May 1993, pp. 518-528, with English language translation.

\* cited by examiner

| PM (1) | EP (1) |
|--------|--------|
| PM (2) | EP (2) |
| PM (3) | EP (3) |
| PM (4) | EP (4) |
| ⋮ | ⋮ |
| PM (N) | EP (N) |

FIG. 12

METHODS AND APPARATUS FOR CALIBRATING RESPIRATORY EFFORT FROM PHOTOPLETHYSMOGRAPH SIGNALS

CROSS REFERENCE TO RELATED APPLICATIONS

Portions of this specification will also be found in Addision et al. U.S. patent application Ser. No. 12/245,366, filed Oct. 3, 2008, which is hereby incorporated by reference herein in its entirety.

SUMMARY OF THE DISCLOSURE

The present disclosure relates to signal processing and, more particularly, the present disclosure relates to using continuous wavelet transforms for processing, for example, a photoplethysmograph (PPG) signal, to determine effort, such as respiratory effort of a patient.

Systems and methods to analyze the suitable signal domain representation in order to determine effort are disclosed herein. In one embodiment, effort may relate to a measure of strength of at least one repetitive feature in a signal. In another embodiment, effort may relate to physical effort of a process that may affect the signal (e.g. effort may relate to work of a process).

In some embodiments, the use of a transform may allow a signal to be represented in a suitable domain such as, for example, a scalogram (in a time-scale domain) or a spectrogram (in a time-frequency domain). A type of effort which may be determined by analyzing the signal representation may be, for example, breathing effort of a patient. The breathing effort of the patient may be determined by analyzing a scalogram with the processes presented in this disclosure.

The determination of effort from a scalogram or any other signal representation is possible because changes in effort induce or change various features of the signal used to generate the scalogram. For example, the act of breathing may cause a breathing band to become present in a scalogram that was derived from a PPG signal. This band may occur at or about the scale having a characteristic frequency that corresponds to the breathing frequency. Furthermore, the features within this band or other bands on the scalogram (e.g., energy, amplitude, phase, or modulation) may result from changes in breathing and/or breathing effort and therefore may be correlated with the patient's breathing effort.

The effort determined by the methods and systems described herein may be represented in any suitable way. For example, breathing effort may be represented graphically in which changes in features of the breathing band and of neighboring bands are represented by changes in color or pattern.

Alternatively, or in combination with the graphical representation, a quantitative value indicative of the relative change in effort or of an absolute value of effort may be calculated according to any suitable metric.

In addition, thresholds may be set to trigger alarms if effort increases (e.g., by percent change or absolute value) over the threshold.

In one embodiment, the present disclosure may be used in the context of a sleep study environment to detect and/or differentiate apneic events. In an embodiment, the present disclosure may be used to monitor the effect of therapeutic intervention.

In accordance with certain possible aspects of the disclosure, a method of calibrating respiratory effort of a patient may include using a pressure sensor to measure air pressure in the patient's oral/nasal cavity during breathing with each of a plurality of successive different amounts of resistance to breathing to produce an oral/nasal pressure signal value for each respective amount of breathing resistance. The method may further include using respiratory effort monitoring apparatus to acquire from the patient an effort signal indicative of the respiratory effort (or breathing effort) the patient exerts or expends during breathing with each respective amount of breathing resistance. The method may still further include using effort signal processing circuitry to determine from the effort signal for each respective amount of breathing resistance a respective breathing effort signal value. For example, the respiratory effort monitoring apparatus may be photoplethysmograph ("PPG") monitoring apparatus for acquiring a PPG signal from the patient. Other examples of respiratory effort monitoring apparatus that can be used include piezobands (e.g., one such band around the patient's chest and another such band around the patient's abdomen), transthoracic impedance measurement across electrocardiogram ("ECG" or "EKG") electrodes on the patient's chest, or any other suitable apparatus for monitoring breathing effort and producing an output signal indicative thereof.

In accordance with a further possible aspect of the disclosure, the above method may further include using storage circuitry to store a correlation between each oral/nasal pressure signal value and the breathing effort signal value concurrent with that respective oral/nasal pressure signal value.

In the above method, each oral/nasal signal value may be produced while the patient is awake.

In a subsequent phase of the above method, the patient may be allowed to sleep, and respiratory effort monitoring apparatus may be used to acquire an effort signal from the sleeping patient. Effort signal processing circuitry may then be used to determine from the last-mentioned effort signal at least one breathing effort signal value for the sleeping patient. The above-mentioned correlation (from the "patient awake" phase of the method) may be used to convert the breathing effort signal value for the sleeping patient to a respiratory system air pressure signal value for the sleeping patient. This respiratory system air pressure signal value may be output in human-readable form.

In the above method, the using effort signal processing circuitry may include producing scalogram signals representing a scalogram of the effort signal, analyzing the scalogram signals to identify breathing band signals in the scalogram signals, and determining a breathing band amplitude signal value as an indication of breathing effort.

The above method may include using breathing resistance apparatus to subject the patient to successive different amounts of resistance to breathing. This may involve applying the breathing resistance apparatus to the patient so that the patient can only breathe through an air flow passageway through the breathing resistance apparatus. In such an embodiment, the method may further include varying the size of the air flow passageway to subject the patient to the successive different amounts of resistance to breathing.

In the above method the using a pressure sensor may include placing the pressure sensor in the patient's mouth.

In accordance with certain other possible aspects of the disclosure, apparatus for monitoring sleep apnea of a patient may include means for subjecting the patient, while awake, to a plurality of different amounts of resistance to breathing. The apparatus may further include means for measuring air pressure in the patient's oral/nasal cavity to determine an air pressure value for each respective amount of resistance to breathing. The apparatus may still further include means for using a respiratory effort signal from the patient to measure the patient's breathing effort to determine a breathing effort value for each respective air pressure value and thereby a relationship between breathing effort and air pressure. Examples of suitable respiratory effort monitoring apparatus have been mentioned in an earlier paragraph and include PPG apparatus, piezo-bands, transthoracic impedance measurement apparatus, and the like. The apparatus may yet further include means for continuing to use the respiratory effort signal from the patient, while asleep, to determine apneic breathing effort values during apneic events. And the apparatus may still further include means for using the above relationship to determine a patient respiratory system air pressure that corresponds to each respective apneic breathing effort value.

In apparatus of the type described above, the means for using a respiratory effort signal may include means for producing scalogram signals representing a scalogram of the effort signal. In such a case, the apparatus may further include means for analyzing the scalogram signals to identify breathing band signals in the scalogram signals. Still further in such a case, the apparatus may include means for determining amplitude of the breathing band signals as an indication of breathing effort.

Apparatus of the type described above may also include means for outputting a human-readable indication of the respiratory system air pressure that corresponds to each apneic breathing effort value.

In apparatus of the kind described above, the means for subjecting may include means for requiring the patient to breath through only an air flow passageway through controllable breathing resistance apparatus. In such a case, the size of the air flow passageway may be variable to vary the amount of breathing resistance the breathing resistance apparatus subjects the patient to.

In apparatus of the kind described above, the means for measuring may include a pressure sensor adapted for placement in the patient's mouth.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which:

FIG. 12 is a simplified schematic block diagram of an illustrative embodiment of an electrical signal data structure in accordance with certain possible aspects of the disclosure.

DETAILED DESCRIPTION

Figure 1:
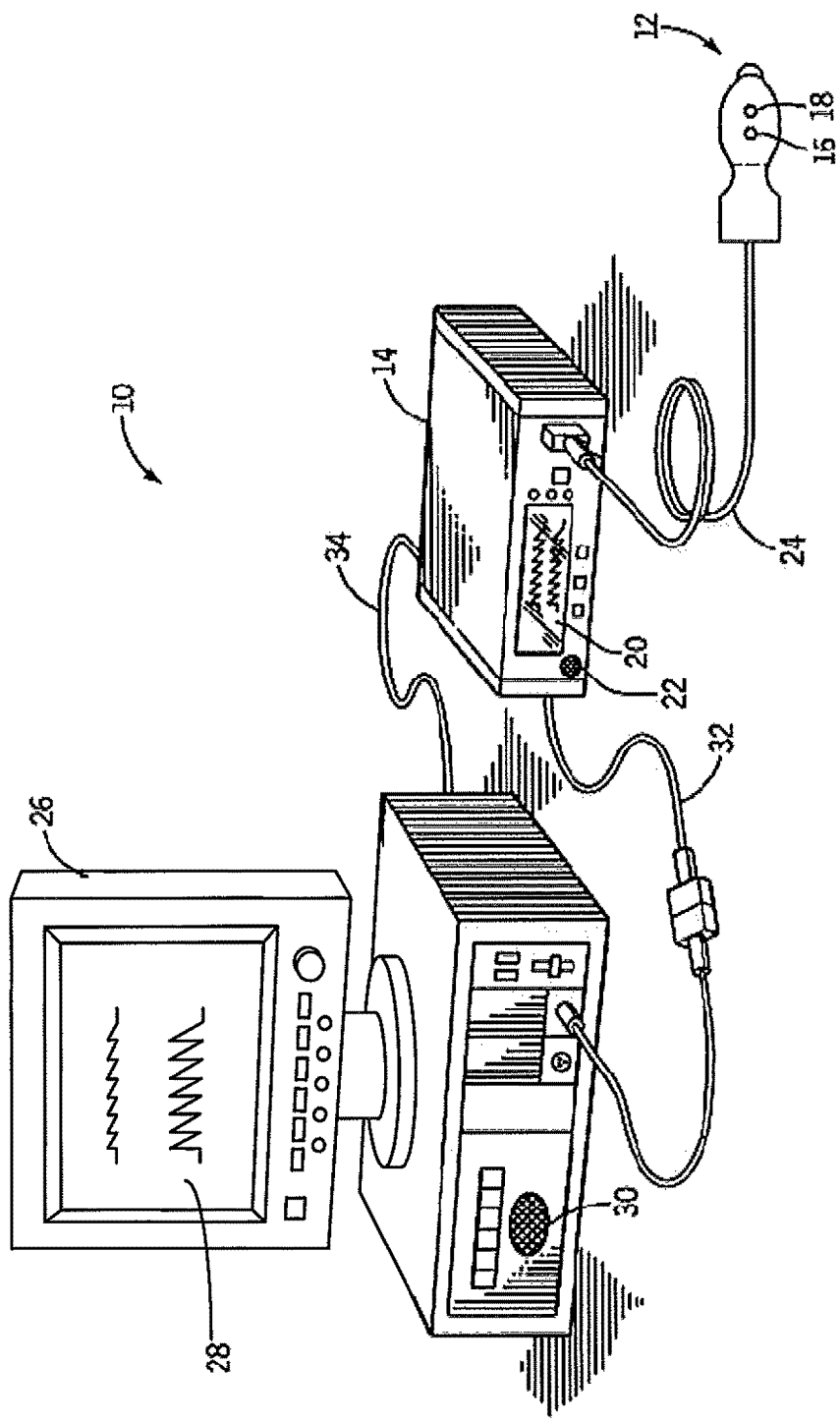
FIG. 1 shows an illustrative effort system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood. Pulse oximeters may also be used to determine respiratory effort in accordance with the present disclosure.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_O(\lambda) \exp(-(s\beta_O(\beta) + (1-s)\beta_r(\lambda))l(t)) \quad (1)$$

where:
$\lambda$=wavelength;
t=time;
I=intensity of light detected;
$I_O$=intensity of light transmitted;
s=oxygen saturation;
$\beta_O, \beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_O - (s\beta_O + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_R)}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda,t)}{dt} \simeq \log I(\lambda,t_2) - \log I(\lambda,t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} = \quad (7)$$

$$\frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)} = R$$

which defines a cluster of points whose slope of y versus x will give R where $x(t)=[I(t_2,\lambda_{IR})-I(t_1,\beta_{IR})]I(t_1,\lambda_R)$ $y(t)=[I(t_2,\lambda_R)-I(t_1,\lambda_R)]I(t_1,\lambda_{IR})$ $$y(t)=Rx(t) \quad (8)$$

FIG. 1 is a perspective view of an embodiment of an effort system 10. In an embodiment, effort system 10 is implemented as part of a pulse oximetry system. System 10 may include a sensor 12 and a monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

Sensor 12 or monitor 14 may further include, but are not limited to software modules that calculate respiration rate, airflow sensors (e.g., nasal thermistor), ventilators, chest straps, transthoracic sensors (e.g., sensors that measure transthoracic impedance).

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the effort or oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, effort system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's respiratory effort or blood oxygen saturation (referred to as an "SpO2" measurement) generated by monitor 14, pulse rate information from monitor 14 and blood pressure from a blood pressure monitor (not shown) on display 28. In the embodiment shown, monitor 26 may also include a speaker 30 similar to speaker 22 described above.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
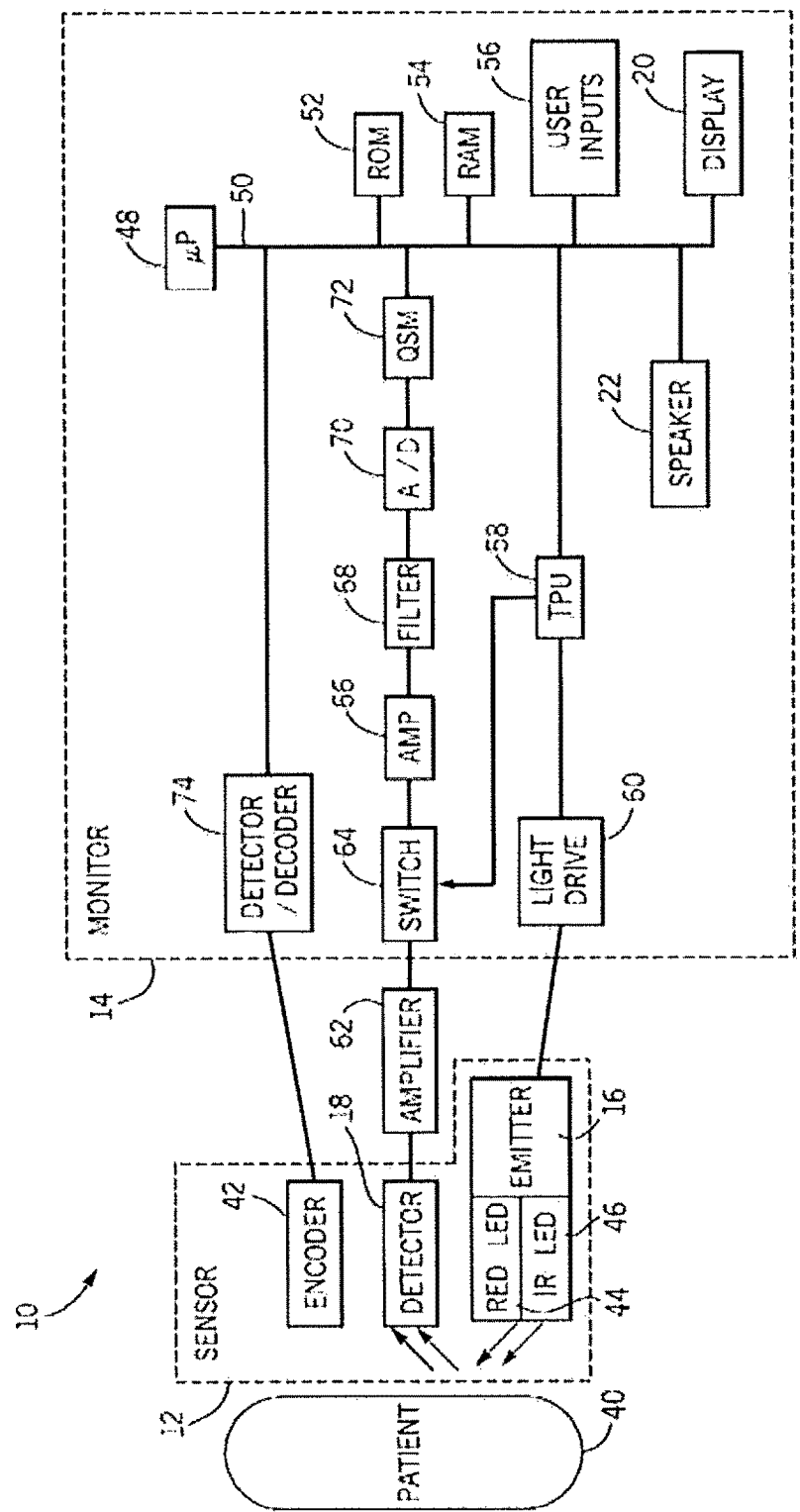
FIG. 2 is a block diagram of the illustrative effort system of FIG. 1 coupled to a patient in accordance with an embodiment.

FIG. 2 is a block diagram of an effort system, such as effort system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit one or more wavelengths of light (e.g., RED and/or IR) into a patient's tissue 40. Hence, emitter 16 may include a RED light emitting light source such as RED light emitting diode (LED) 44 and/or an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as effort, SpO$_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing effort and pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t) \psi^* \left( \frac{t-b}{a} \right) dt \qquad (9)$$

where $\psi^*(t)$ is the complex conjugate of the wavelet function $\psi^*(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \tag{10}$$

where '||' is the modulus operator. The scalogram may be rescaled for useful purposes. One common rescaling is defined as $$S_R(a, b) = \frac{|T(a, b)|^2}{a} \tag{11}$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \tag{12}$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{1/4}(e^{i2\pi f_0 t}-e^{-(2\pi f_0)^2/2})e^{-t^2/2} \tag{13}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \tag{14}$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figures 3A, 3B:
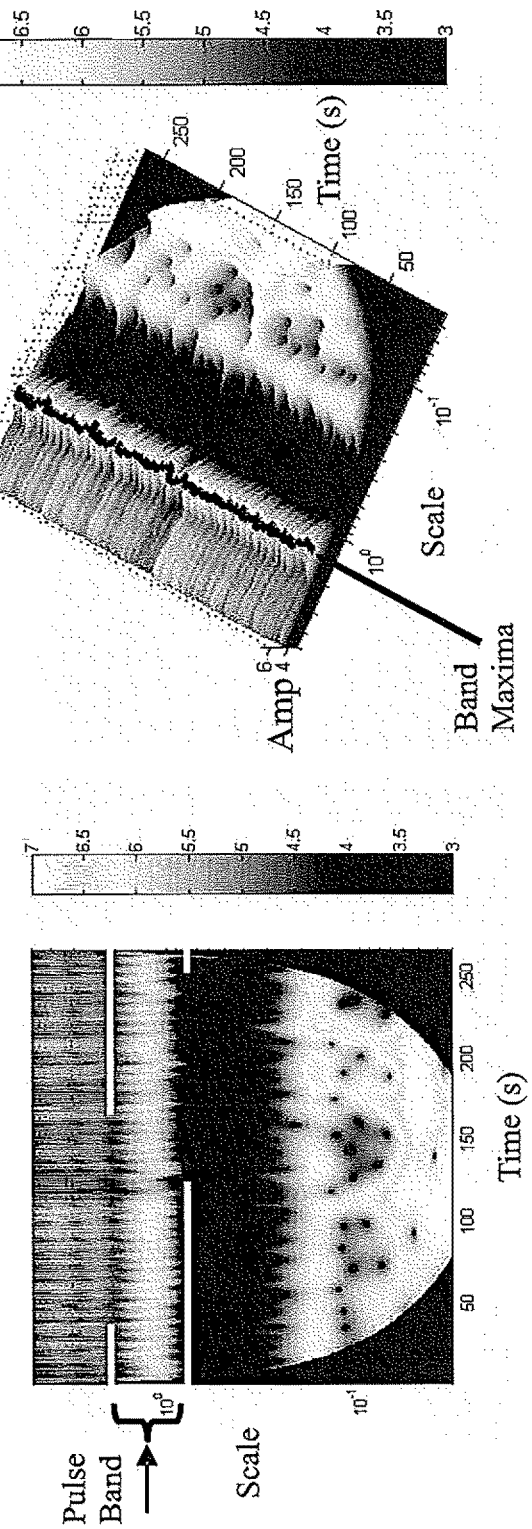
FIGS. 3(a) and 3(b) show illustrative views of a scalogram derived from a PPG signal in accordance with an embodiment.

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
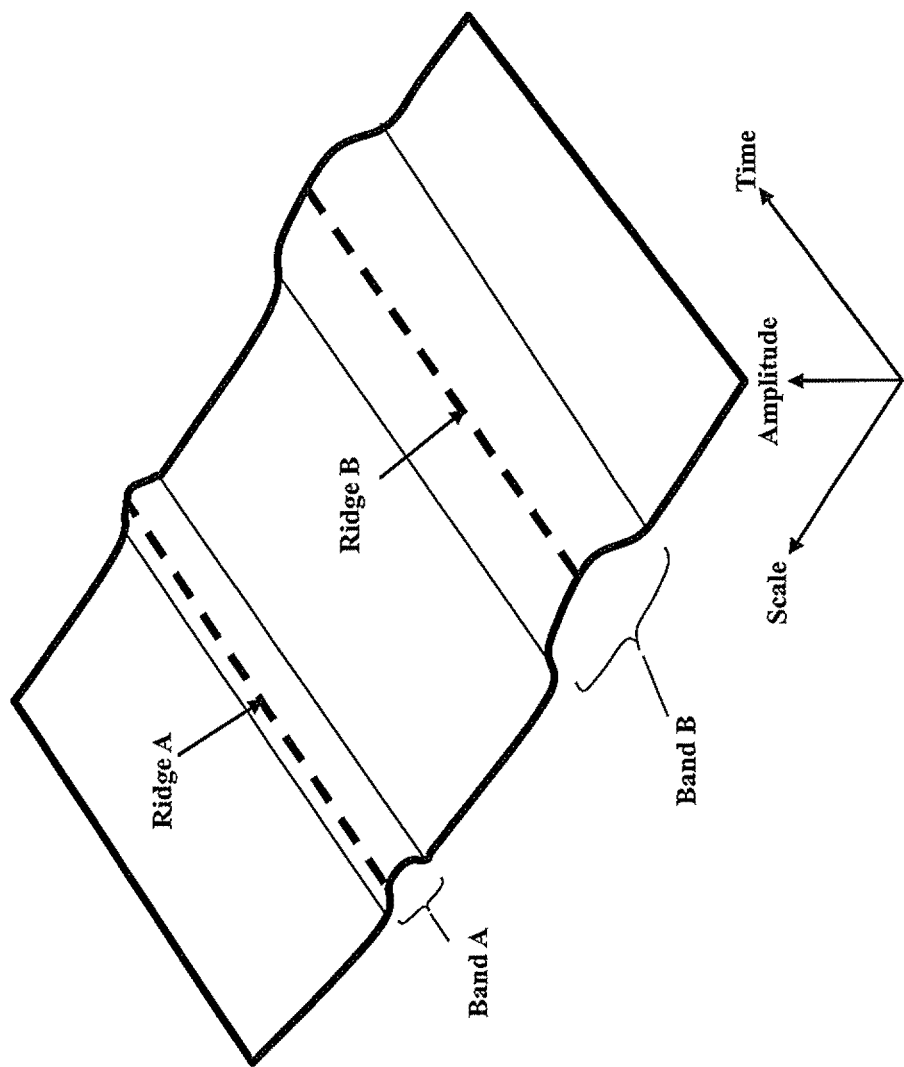
FIG. 3(c) shows an illustrative scalogram derived from a signal containing two pertinent components in accordance with an embodiment.
Figure 3D:
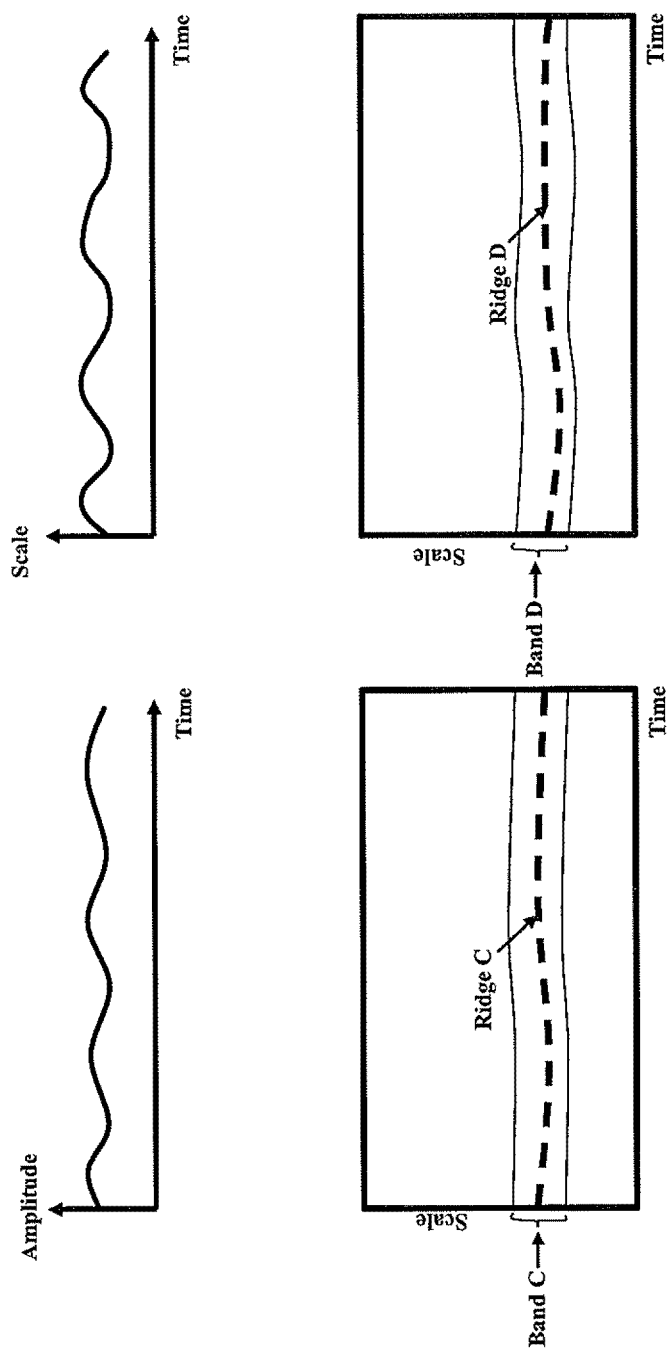
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a, b) \frac{1}{\sqrt{a}} \psi\left(\frac{t-b}{a}\right) \frac{da\,db}{a^2} \tag{15}$$

which may also be written as:

$$x(t) = \frac{1}{C_g} \int_{-\infty}^{\infty} \int_{0}^{\infty} T(a, b) \psi_{a,b}(t) \frac{da\,db}{a^2} \tag{16}$$

where $C_g$ is a scalar value known as the admissibility constant. It is wavelet type dependent and may be calculated from:

$$C_g = \int_{0}^{\infty} \frac{|\hat{\psi}(f)|^2}{f} df \tag{17}$$

Figure 3E:
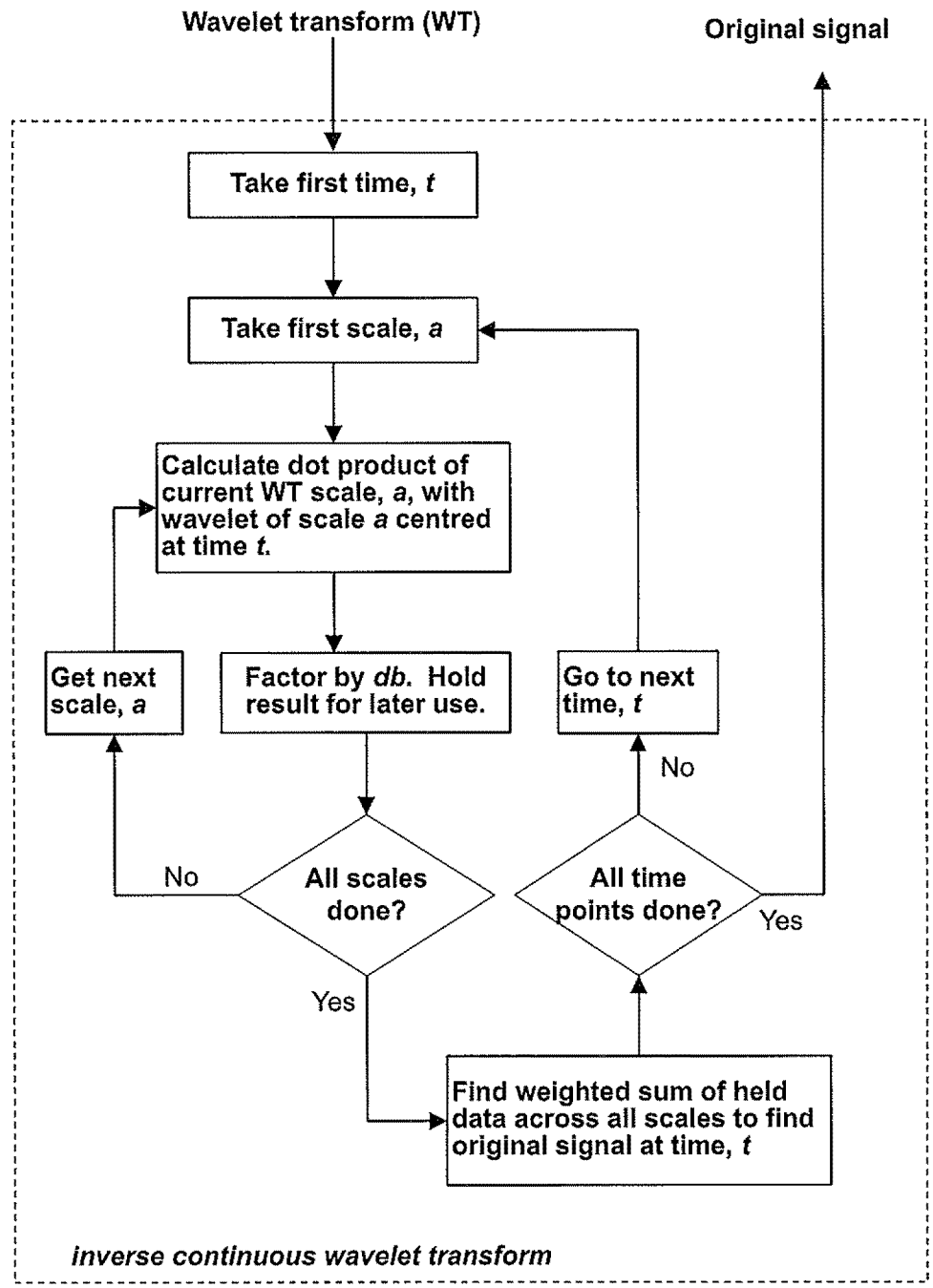
FIGS. 3(e) and 3(f) are flow charts of illustrative steps involved in performing an inverse continuous wavelet transform in accordance with embodiments.
Figure 3F:
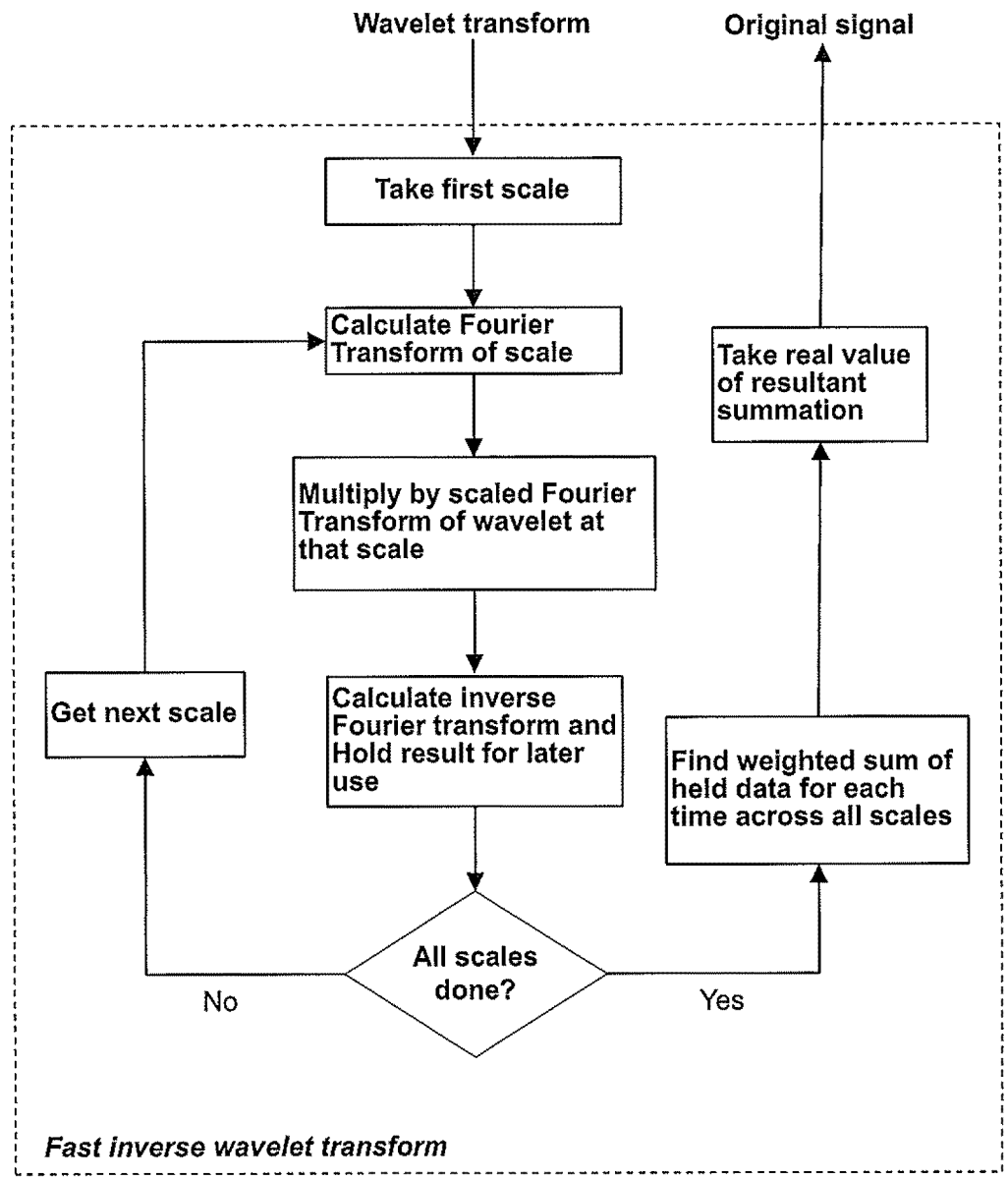

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for processing a signal using the above mentioned techniques and analyzing the results of the techniques to determine effort. In one embodiment, effort may relate to a measure of strength of at least one repetitive feature in a signal. In another embodiment, effort may relate to physical effort of a process that may affect the signal (e.g. effort may relate to work of a process). For example, effort calculated from a PPG signal may relate to the respiratory effort of a patient. Respiratory effort may increase, for example, if a patient's respiratory pathway becomes restricted or blocked. Conversely, respiratory effort may decrease as a patient's respiratory pathway becomes unrestricted or unblocked. The effort of a signal may be determined, for example, by transforming the signal using a wavelet transform and analyzing features of a scalogram derived from the wavelet transform. In particular, changes in the features of the pulse band and breathing band in the scalogram may be correlated to a change in breathing effort.

As an additional example, the methods and systems disclosed herein may be used to determine effort in a mechanical engine. Over time, a mechanical engine may become less efficient because of wear of the mechanical parts and/or insufficient lubrication. This may cause extra strain on the engine parts and, in particular, cause the engine to exert more effort, work, or force to complete a process. Engine function may be monitored and represented using signals. These signals may be transformed and analyzed to determine effort using the techniques described herein. For example, an engine may oscillate in a particular manner. This oscillation may produce a band or bands within a scalogram. Features of this band or bands may change as the engine exerts more or less effort. The change in the features may then be correlated to effort.

It will be understood that the present disclosure is applicable to any suitable signals and that PPG signals or mechanical monitoring signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

The methods for determining effort described in this disclosure may be implemented on a multitude of different systems and apparatuses through the use of human-readable or machine-readable information. For example, the methods described herein maybe implemented using machine-readable computer code and executed on a computer system that is capable of reading the computer code. An exemplary system that is capable of determining effort is depicted in FIG. 4.

Figure 4:
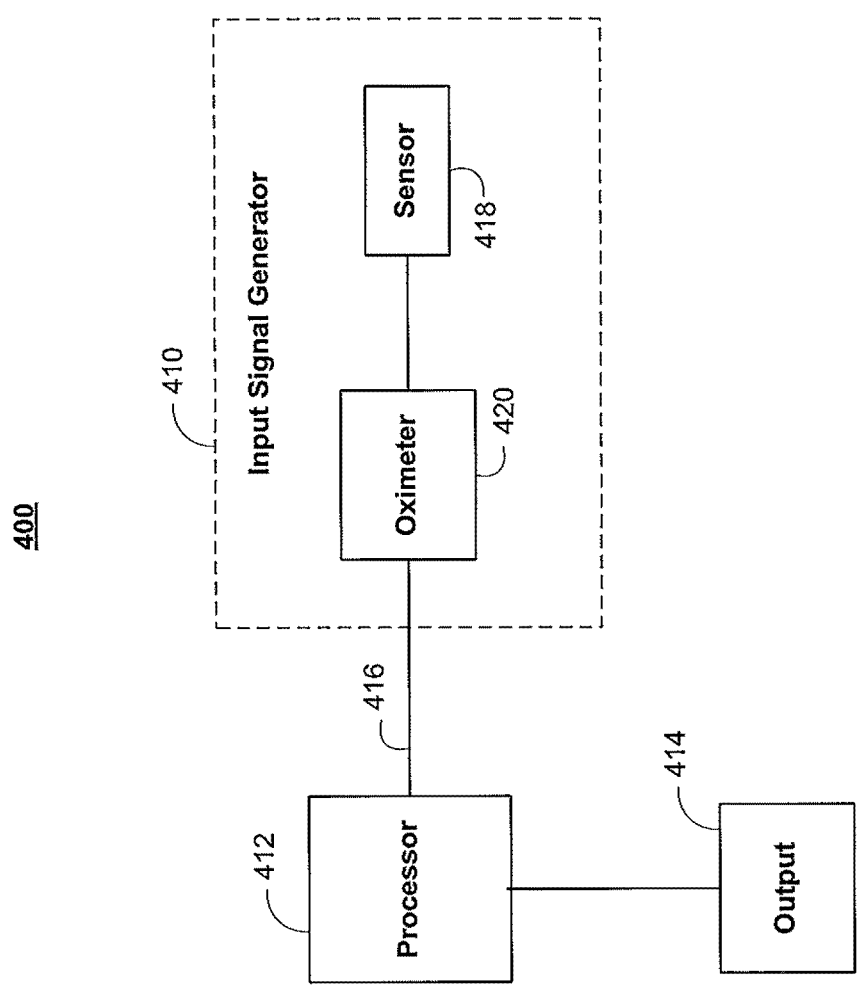
FIG. 4 is a block diagram of an illustrative continuous wavelet processing system in accordance with some embodiments.

FIG. 4 is an illustrative continuous wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In some embodiments, in order to determine effort, processor 412 may first transform the signal into any suitable domain, for example, a Fourier, wavelet, spectral, scale, time, time-spectral, time-scale domains, or any transform space. Processor 412 may further transform the original and/or transformed signals into any of the suitable domains as necessary.

Processor 412 may represent the original or transformed signals in any suitable way, for example, through a two-dimensional representation or three-dimensional representation, such as a spectrogram or scalogram.

After processor 412 represents the signals in a suitable fashion, processor 412 may then find and analyze selected features in the signal representation of signal 416 to determine effort. Selected features may include the value, weighted value, or change in values with regard to energy, amplitude, frequency modulation, amplitude modulation, scale modulation, differences between features (e.g., distances between ridge amplitude peaks within a time-scale band).

For example, selected features may include features in a time-scale band in wavelet space or a rescaled wavelet space described above. As an illustrative example, the amplitude or energy of the band may be indicative of the breathing effort of a patient when the band is the patient's breathing band. Furthermore, changes in the amplitude or energy of the band may be indicative of a change in breathing effort of a patient. Other time-scale bands may also provide information indicative of breathing effort. For example, amplitude modulation, or scale modulation of a patient's pulse band may also be indicative of breathing effort. Effort may be correlated with any of the above selected features, other suitable features, or any combination thereof.

The selected features may be localized, repetitive, or continuous within one or more regions of the suitable domain space representation of signal 416. The selected features may not necessarily be localized in a band, but may potentially be present in any region within a signal representation. For example, the selected features may be localized, repetitive, or continuous in scale or time within a wavelet transform surface. A region of a particular size and shape may be used to analyze selected features in the domain space representation of signal 416. The region's size and shape may be selected based at least in part on the particular feature to be analyzed. As an illustrative example, in order to analyze a patient's breathing band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. For example, the expected locations may be based at least in part on empirical data of a plurality of patients. The region may also be selected based at least in part on patient classification. For example, an adult's breathing band location generally differs from the location of a neonatal patient's breathing band. Thus, the region selected for an adult may be different than the region selected for a neonate.

In some embodiments, the region may be selected based at least in part on features within a scalogram. For example, the scalogram for a patient may be analyzed to determine the location of the breathing band and its corresponding ridge. The breathing band ridge may be located using standard ridge detection techniques. Ridges may also be detected using the techniques described in Watson et al., U.S. application Ser. No. 12/245,326, filed Oct. 3, 2008, entitled "Systems and Methods for Ridge Selection in Scalograms of Signals," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, the region may be determined based at least in part on the repetitive nature of the selected features. For example, a band may have a periodic feature. The period of the feature may be used to determine bounds of the region in time and/or scale.

The size, shape, and location of the one or more regions may also be adaptively manipulated using signal analysis. The adaptation may be based at least in part on changing characteristics of the signal or features within the various domain spaces.

As a signal is being processed, for example by processor 412, the region may be moved over the signal in any suitable domain space over any suitable parameter in order to determine the value or change in value of the selected features. The processing may be performed in real-time or via a previously recorded signal. For example, a region may move over the breathing band in the time-scale domain over time. When the selected features have been analyzed, they may be correlated with effort over time, and hence show the value or change in value of effort over time.

In some embodiments, the determined effort may be provided as a quantitative or qualitative value indicative of effort. The quantitative or qualitative value may be determined using the value or change in values in one or more suitable metrics of relevant information, such as the selected features mentioned above. The quantitative or qualitative values may be based on an absolute difference from a baseline or a calibrated value of the features. For example, breathing effort of a patient may be calibrated upon initial setup. Alternatively, the values may be indicative of a relative change in the features such as the change in distance between peaks in amplitude, changes in magnitude, changes in energy level, or changes in the modulation of features.

The quantitative or qualitative value of effort may be provided to be displayed on a display, for example on display 28. Effort may be displayed graphically on a display by depicting values or changes in values of the determined effort or of the selected features described above. The graphical representation may be displayed in one, two, or more dimensions and may be fixed or change with time. The graphical representation may be further enhanced by changes in color, pattern, or any other visual representation.

The depiction of effort through a graphical, quantitative, qualitative representation, or combination of representations may be presented on output 414 and may be controlled by processor 412.

In some embodiments, a display and/or speaker on output 414 may be configured to produce visual and audible alerts, respectively, when effort rises above or falls below some quantitative or qualitative threshold value. Visual alerts may be displayed on, for example, display 28 and audible alerts may be produced on, for example, speaker 22. The threshold value may be based at least in part on empirical data, baseline readings, average readings, or a combination of data. The threshold value may be configured at the start of operation or configured during operation. In some embodiments, processor 412 may determine whether or not to produce visual, audible, or combination of alerts. The alerts may be triggered if effort rises above or falls below the threshold value by a particular percentage change or absolute value change.

The analysis performed above that leads to a value of determined effort and/or an alert may also be used to detect events based at least in part on determined effort and/or other detected features. For example, this process may be used in connection with sleep studies. Increased effort may be used to detect and/or differentiate apneic events from other events. For example, reduced effort may indicate a central apnea and increased effort may indicate an obstructive apnea. In an embodiment, respiration effort from a PPG signal may be used in combination with other signals typically used in sleep studies. In one embodiment, the present disclosure may be used to monitor the effect of therapeutic intervention, for example, to monitor the effect of asthmatic drugs on a patient's respiratory effort. For example, a patient's respiratory effort may be monitored to determine how quickly the patient's respiratory effort reduces over time, if at all, after the patient receives a drug to relieve the symptoms of asthma.

Figure 5:
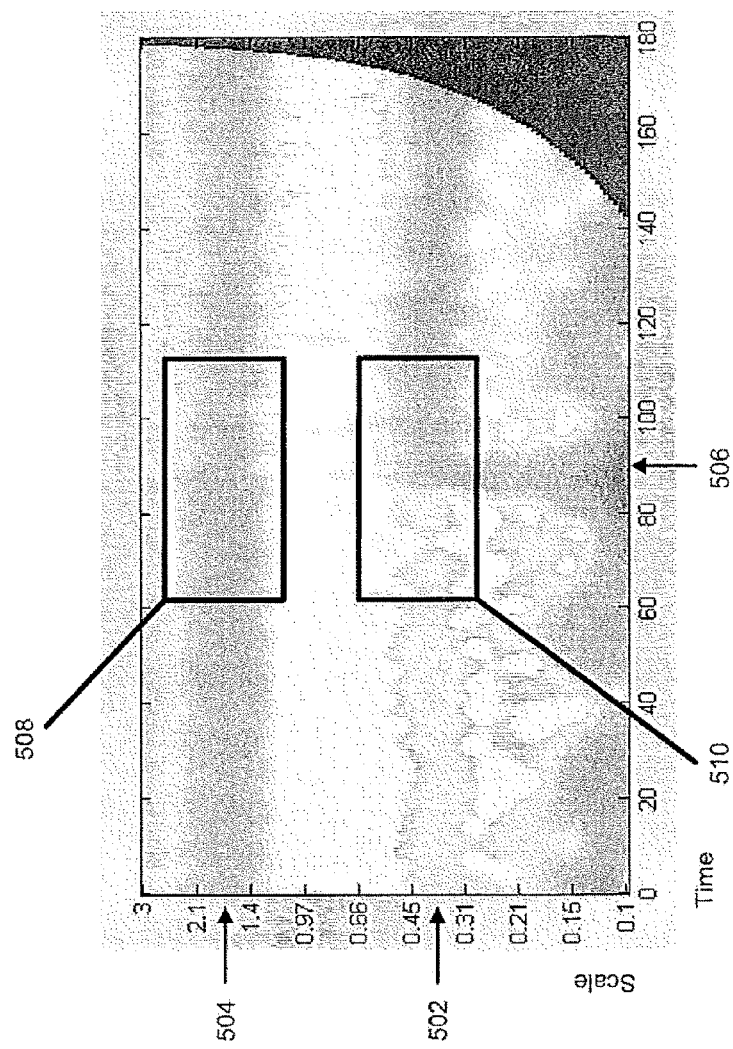
FIG. 5 is an illustrative scalogram showing the manifestation of a plurality of bands and an increase in effort in accordance with some embodiments.

FIG. 5 shows an illustrative scalogram of a PPG signal that may be analyzed in accordance with an embodiment of the disclosure. The scalogram may be produced by system 10 of FIGS. 1 and 2 or system 400 of FIG. 4 as described above. The scalogram as shown includes breathing band 502 and pulse band 504. These bands may be found and analyzed for features that may be indicative of breathing effort.

FIG. 5 shows an increased respiratory effort beginning at time 506, which may be caused by a patient experiencing increased breathing resistance. In order to detect this change in respiration effort, regions 508 and 510 may be used. Region 508 is generally located over a portion of pulse band 504 and region 510 is generally located over a portion of breathing band 502. Regions 508 and 510 may be shifted across the scalogram over time, allowing the features within the regions to be analyzed over time. The size, shape, and locations of regions 508 and 510 are merely illustrative. The features of the regions may be changed as they are shifted and any other suitable size, shape, and location may be used as described above.

At time 506, it may be observed that the modulation of the amplitude and scale of pulse band 504 may begin to increase (e.g., within region 508). Analysis of this modulation or change of this modulation, as described above, may be correlated to the patient's breathing effort because increased respiration effort may lead to this increase in amplitude and scale modulation of the pulse band. The modulation may be determined by analyzing, for example, the modulation of the ridge of the pulse band.

Increased respiration effort may also lead to increased amplitude and energy of the breathing band 502. The increase in amplitude and energy can be seen within region 510 at time 506. The amplitude may be determined by analyzing the ridge of the respiration band. The energy may be determined by analyzing the average or median energy within region 510. Analysis of the amplitude and/or energy or change in amplitude and/or energy within region 510 may also be correlated to the patient's breathing effort.

The patient's breathing effort may be determined based at least in part on the amplitude modulation, scale modulation, the amplitude, or the energy of the respiration band or the pulse band, or changes in those features, or any suitable combination thereof.

It will be understood that the above techniques for analyzing a patient's breathing effort can be used to determine any kind of effort. For example, these techniques can be used to determine the effort associated with any biological process, mechanical process, electrical process, financial process, geophysical process, astronomical process, chemical process, physical process, fluid process, speech process, audible process, meterological process, and/or any other suitable process, and/or any combination thereof.

As an additional example, the above techniques may be used to determine effort in a mechanical engine. Engine function may be monitored and represented using signals. These signals may be transformed and represented by, for example, a scalogram. Normal engine function may produce a band or bands within the scalogram. Features of this band or bands may change or become apparent as the engine exerts more or less effort. These features may include changes in the amplitude modulation, scale modulation, the amplitude, or energy of the bands. These features may also change or become apparent in other regions of the scalogram. The appearance or change in these features may then be correlated to effort or change in effort exerted by the engine.

It will also be understood that the above techniques may be implemented using any human-readable or machine-readable instructions on any suitable system or apparatus, such as those described herein.

Figure 6:
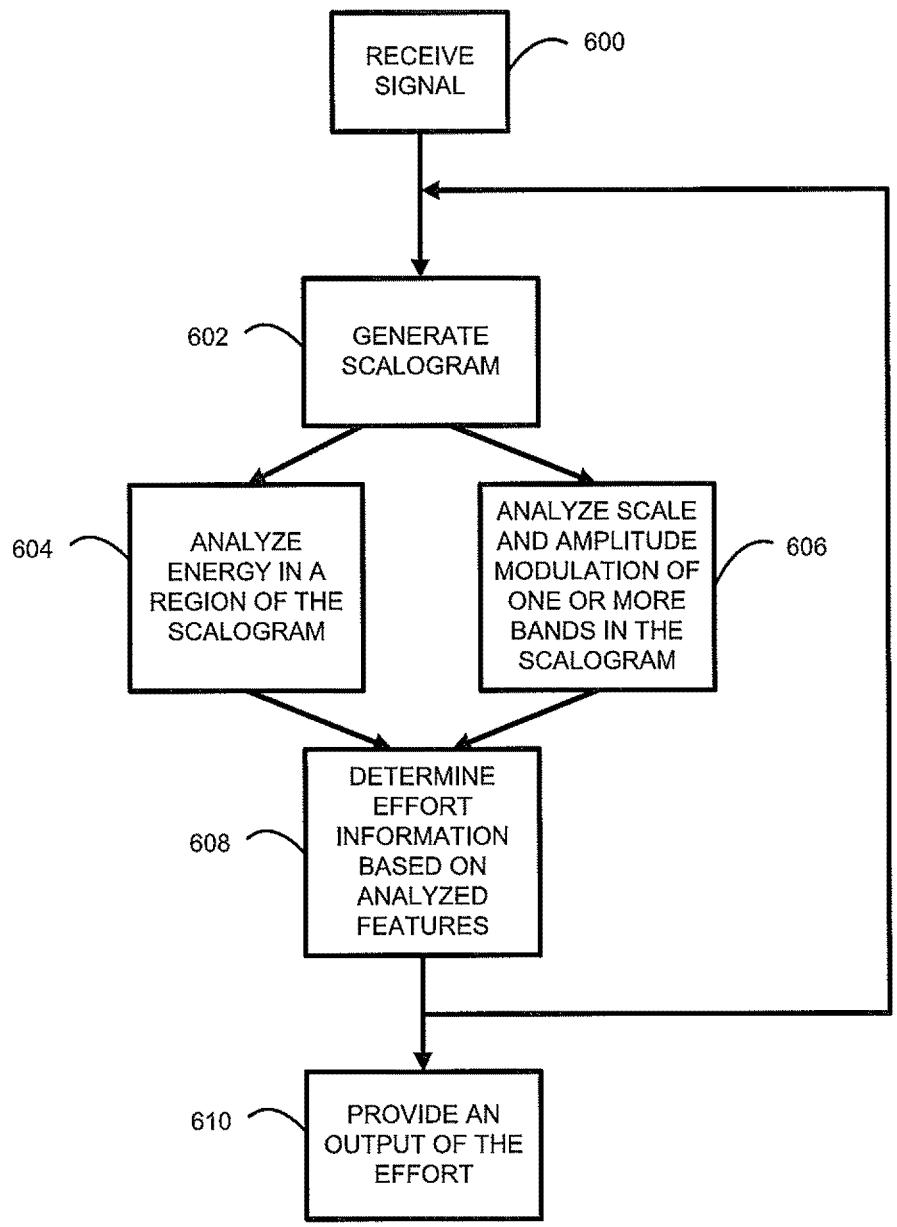
FIG. 6 is an illustrative flow chart depicting the steps used to determine effort in accordance with some embodiments.

FIG. 6 is an illustrative flow chart depicting the steps that may be used to determine effort. In step 600, one or more signals may be received, including, for example, one or more biosignals (e.g., electrocardiogram, electroencephalogram, electrogastrogram, electromyogram, heart rate signals, pathological sounds, ultrasound, or any other suitable biosignal), physiological signals, dynamic signals, non-destructive testing signals, condition monitoring signals, fluid signals, geophysical signals, physical signals, astronomical signals, electrical signals, electromagnetic signals, mechanical signals, financial signals including financial indices, sound and speech signals, chemical signals, meteorological signals including climate signals, and/or any other suitable signal, and/or any combination thereof. As an illustrative example, the input signal may be a PPG signal.

In step 602, the received signal(s) may be transformed into any suitable domain, such as a Fourier, wavelet, spectral, scale, time, time-spectral, or time-scale domain. For example, the signal(s) may be transformed into a time-scale domain using a wavelet transform such as a continuous wavelet transform. Once the signal is transformed into a suitable domain, it may be depicted by a suitable representation. Suitable representations may include two-dimensional or three-dimensional representations. As an illustrative example, the signal transformed into the time-scale domain and then may be represented by a scalogram.

Once the signal is transformed and represented by a suitable representation, one or more features may be analyzed within the signal representation as shown in steps 604 and 606.

In steps 604 and 606, one or more regions within the signal representation may be chosen for inspection. These regions may be similar to region 508 and region 510. As stated above with respect to region 508 and region 510, the regions may be comprised of any suitable size, shape, and location. They also may be shifted across the scalogram over time, allowing features within the regions to be analyzed over time. For example, the regions may cover bands within a scalogram such as a pulse band or a respiration band. The regions may also cover any other suitable bands or features within the signal representation.

In step 604, the features analyzed within a region may include amplitude or energy. In step 606, amplitude modulation, scale or frequency modulation, distances between peaks, and/or any other suitable features and/or combination of features may be analyzed.

In step 608, effort information may be determined based at least in part on the analysis of the features in steps 604 and 608. As described above with respect to FIG. 5, effort may be correlated with changes or the appearance of the features found and analyzed in steps 604 and 606. For example, breathing effort may be correlated with a change or weighted change in amplitude, energy, amplitude modulation, frequency modulation, and/or scale modulation in the breathing and/or pulse bands. The correlation between effort and the analyzed features may be used to determine quantitative or qualitative values associated with effort. The determined values may, for example, indicate effort or a change of effort. The values may be determined based at least in part on an absolute or percentage difference from a baseline or calibrated value of effort. Furthermore, the values may be determined based at least in part on changes or appearance of the analyzed features within the signal representation.

The analysis performed in step 608 may also determine whether the determined effort has risen above or fallen below a threshold value. The threshold value may be based at least in part on empirical data, baseline readings, average readings, or a combination of data. The threshold value may be configured based at least in part on effort or features at the start of operation or may be adjusted during operation. If effort crosses a threshold value, an alert may be issued. In some embodiments, the alert may be triggered if effort rises above or falls below a threshold value by a particular percentage change, absolute value change, or if the determined effort value crosses the threshold value.

The analysis performed in step 608 may also detect events based at least in part on determined effort and/or other detected features. For example, this process may be used in connection with sleep studies. Increased effort may be used to detect and/or differentiate apneic events from other events. If such an apneic event occurs, an additional notification may be generated. In an embodiment, respiration effort from a PPG signal may be used in combination with other signals typically used in sleep studies.

In step 610, the signal analysis and determined effort may be output along with a possible alert if an alert has been triggered. The output may be displayed on a display, such as display 28 shown in FIG. 1. A graphical display may be generated based at least in part on the determined qualitative or quantitative values representing effort or changes in effort. The graphical representation may be displayed in one, two, or more dimensions and may be fixed or change with time. The graphical representation may be further enhanced by changes in color, pattern, or any other visual representation. Additionally, the alert may be made visual by being displayed on a display, for example display 28, or may be made through an audible sound on a speaker, for example speaker 22.

As the signal analysis and determined effort are being output in step 610, the whole process may repeat. Either a new signal may be received, or the effort determination may continue on another portion of the received signal(s). The process may repeat indefinitely, until there is a command to stop the effort determination, and/or until some detected event occurs that is designated to halt the effort determination process. For example, it may be desirable to halt effort determination after a sharp increase in breathing effort is detected.

It will also be understood that the above method may be implemented using any human-readable or machine-readable instructions on any suitable system or apparatus, such as those described herein.

Figure 7:
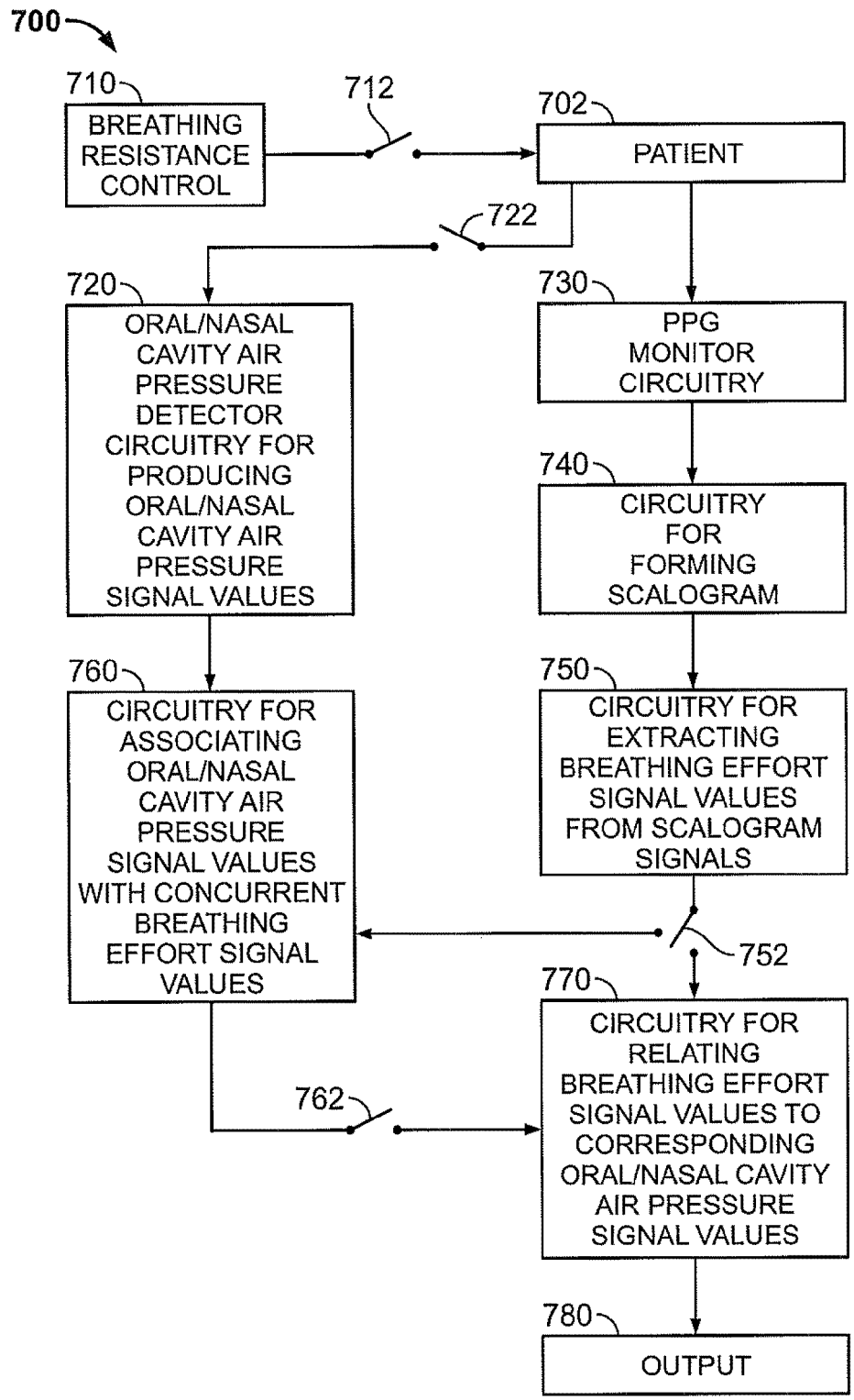
FIG. 7 is a simplified schematic block diagram of an illustrative embodiment of apparatus in accordance with certain possible aspects of the disclosure.

An illustrative embodiment of apparatus 700 for calibrating respiratory effort information in accordance with certain possible aspects of the present disclosure is shown in FIG. 7. The FIG. 7 embodiment employs photopleth-symograph ("PPG") apparatus to measure the effort a patient is exerting in order to breathe. It will be understood, however, that this is only illustrative, and that other respiratory effort monitoring apparatus may be used instead if desired. Examples of such other apparatus include piezo-bands, transthoracic impedance measurement (e.g., across electrocardiogram electrodes on the patient's chest), or other suitable apparatus. For the most part, the following discussion will refer to the PPG example. But, again, it will be understood that this is only an example, and other ways of measuring a patient's respiratory effort may be used instead if desired.

One purpose of apparatus 700 may be to calibrate respiratory effort information gathered by analysis of (for example) PPG signals in other terms such as air pressure in a patient's respiratory system. In other words, one or more values of respiratory effort EP(i) (as determined by analysis of PPG signals) may each be related to (or correlated with) a value PM(i) of air pressure in the patient's respiratory system measured during collection of the PPG signal information that led to respiratory effort value EP(i). After such initial calibration of the respiratory effort information, that correlation with respiratory system air pressure can be used to infer an air pressure value for any subsequently measured value of respiratory effort (e.g., EP(a), determined from analysis of subsequent PPG signals). For example, the correlation between EP(i) and PM(i) may be determined while the patient is awake. Thereafter, when the patient is asleep and an apneic event occurs, the resulting respiratory effort value EP(a) can be translated to a corresponding respiratory system air pressure value PM(a) using the previously determined correlation or relationship between EP(i) and PM(i). (Although "patient 702" is included in FIG. 7 for completeness, it will be understood that the patient is not part of apparatus 700 or the present disclosure. Apparatus 700 is suitable for use, for example, for a patient 702 undergoing a sleep laboratory study.)

Figure 8:
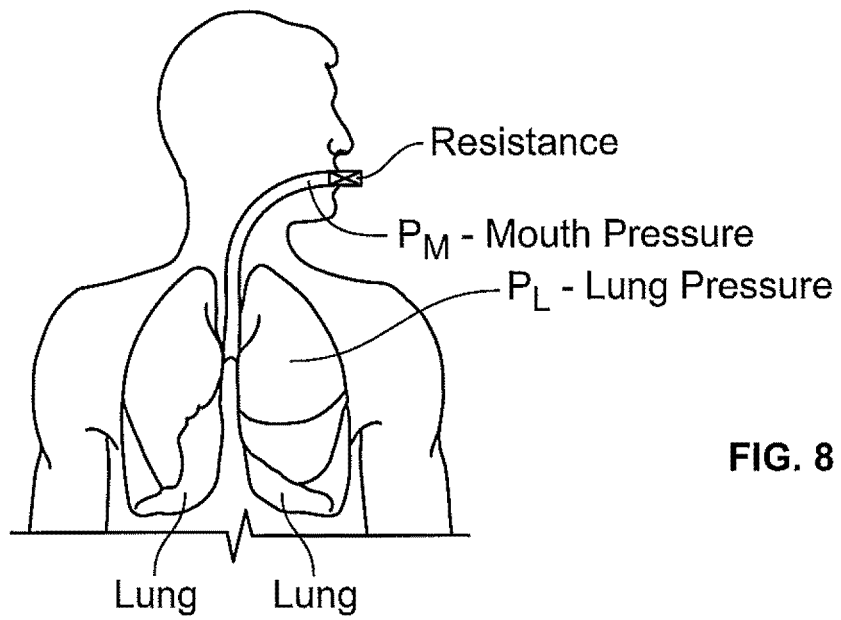
FIG. 8 is a simplified schematic diagram of typical patient anatomy to which certain components of the disclosure (illustratively embodied) have been applied.

As shown in FIG. 7, apparatus 700 includes breathing resistance control apparatus 710, which can be connected to patient 702 via schematically indicated connector or connection 712 while the patient is awake. Breathing resistance control apparatus 710 may be any apparatus through which the patient must breathe with a selectable (controllable) amount of resistance to such breathing. For example, apparatus 710 may be a full face mask over the mouth and nose of patient 702 with a small opening for air flow. This small opening may be adjustable in size to increase or decrease the resistance to breathing that apparatus 710 offers to patient 702. Other types of resistance 710 may also be used. For example, the patient's nose may be sealed off and the patient made to breathe through a tube held in or otherwise secured to the patient's mouth. This tube may have controllably variable degrees of closure. This is shown schematically in FIG. 8. However apparatus 710 is constructed, schematic connection 712 is closed when the patient is fitted with apparatus 710;

and connection 712 is open when apparatus 710 is removed from the patient. Indeed, connection 712 may represent nothing more than fitting the patient with apparatus 710 (connection closed) or removal of apparatus 710 from the patient (connection open).

Continuing with FIG. 7, patient 702, while awake, is also connected to oral/nasal cavity air pressure detector circuitry 720. This connection 722 may be the result of placing an air pressure sensor or transducer in the patient's mouth (e.g., at the point indicated by PM in FIG. 8). Schematically indicated connection 722 is closed when such a sensor is present in the patient's mouth and connected to apparatus 720. Connection 722 is open when the pressure sensor is removed from the patient's mouth or otherwise disconnected from apparatus 720. It is assumed for present purposes that air pressure in the patient's nose and mouth is generally the same, and that "oral/nasal cavity" is a more general term than either nose or mouth alone. Hence a measure of air pressure in the patient's mouth (or anywhere else in the patient's oral/nasal cavity such as in the nose) can be taken as a good indicator of air pressure anywhere in the patient's oral/nasal cavity. As used herein, oral/nasal cavity means the nose and/or the mouth and/or the patient-interior passageways (toward the back of the nose and mouth) that effect pneumatic connection between the nose and the mouth.

Figure 9A:
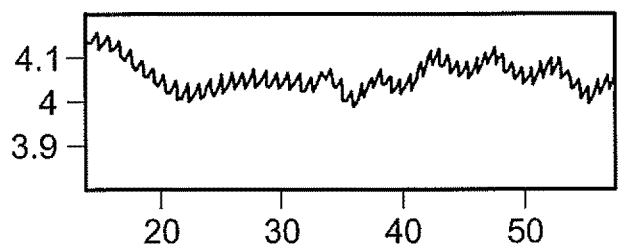
FIG. 9a is a simplified depiction of a typical photoplethysmograph ("PPG") signal waveform from a patient in accordance with certain possible aspects of the disclosure.

FIG. 7 also shows patient 702 connected to PPG monitor circuitry 730. This connection preferably exists at all relevant times, and so it is not thought necessary to show it as being made through a selectively closable or openable connection like 712 or 722. PPG monitor circuitry 730 can be like any PPG monitor circuitry shown and described elsewhere in this specification. PPG monitor circuitry 730 produces a PPG signal indicative of aspects of the patient's condition that circuitry 730 can capture from the patient and output in the PPG signal, all as described earlier in this specification. For example, FIG. 9a shows an example of a PPG signal for a patient whose breathing is unrestricted up to about 30 seconds, after which the patient continues to breathe against a selected amount of resistance (this amount of breathing resistance being associated with a current value of an index i).

Circuitry 730 applies the PPG signal it produces to circuitry 740. Circuitry 740 can be any circuitry for forming scalogram signals from the PPG signal as shown and described earlier in this specification.

Figure 9B:
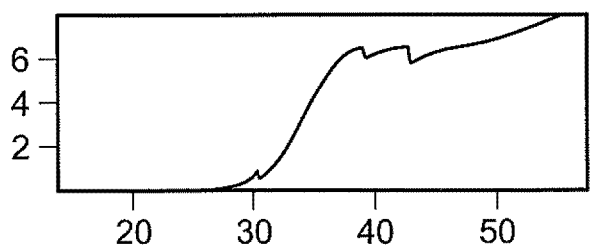
FIG. 9b is a simplified depiction of a typical waveform of certain information extracted from the FIG. 9a signal in accordance with certain possible aspects of the disclosure (FIGS. 9a and 9b are plotted against the same time scale and are shown synchronized in time with one another)

The scalogram signals produced by circuitry 740 are processed by circuitry 750 to extract breathing effort signal values from the scalogram signals. Once again, circuitry 750 can be as shown and described earlier in this specification. FIG. 9b shows a plot of breathing effort ridge amplitude vs. time (using the same horizontal time scale as (and synchronized with) FIG. 9a). The information shown in FIG. 9b can be a plot (vs. time) of breathing effort signal values collected by circuitry 750 over time. During this phase of the operation of apparatus 700, circuitry 750 can make the breathing effort signal values it extracts available to circuitry 760 via connection 752 (which, during this time, is arranged to apply the outputs of circuitry 750 to circuitry 760 (rather than to circuitry 770)).

Figure 10:
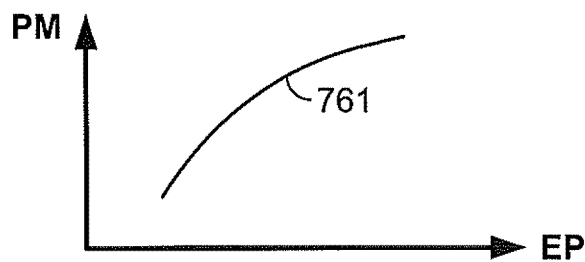
FIG. 10 is a simplified depiction of an illustrative correlation between two variables in accordance with certain possible aspects of the disclosure.

Circuitry 760 also receives concurrent oral/nasal cavity air pressure signal values from circuitry 720. Accordingly, circuitry 760 can relate various values of oral/nasal cavity air pressure PM(i) (received from circuitry 720) to concurrently received values of breathing effort EP(i) (received from circuitry 750). Circuitry 760 stores (e.g., in a memory table) the data for each such relationship of breathing effort relative to oral/nasal cavity air pressure. After a sufficient number of breathing effort values have been collected at different breathing resistance values (and therefore at different oral/nasal air pressure values), the information stored in circuitry 760 may be something like the relationship shown in FIG. 10, in which the horizontal axis represents breathing effort (from circuitry 750), and the vertical axis represents oral/nasal air pressure (from circuitry 720). The curve 761 shown in FIG. 10 is thus a typical correlation between breathing effort and oral/nasal cavity air pressure determined by apparatus 700 and stored for future reference in circuitry 760. (It will of course be understood that the particular curve 761 shown in FIG. 10 is only an example, and that each patient 702 is likely to have a curve 761 that differs in at least some respects from the curves for other patients.)

When apparatus 700 has been operated with enough different values of breathing resistance (provided by apparatus 710) to enable circuitry 760 to have collected information for a sufficiently well-developed correlation 761 as shown in FIG. 10, the "patient awake" phase of the procedure can be ended. This means opening connection 712 (e.g., removing breathing resistance control apparatus 710 from the patient), opening connection 722 (e.g., removing the air pressure detector from the patient), switching connection 752 from (1) connecting circuitry 750 to circuitry 760 to (2) connecting circuitry 750 to circuitry 770, and closing connection 762. Patient 702 can now be allowed to sleep and apparatus 700 enters its "patient asleep" phase of operation.

While the patient sleeps, elements 710 and 720 are not used, but elements 730, 740, and 750 continue to operate (or again operate) as described above for the "patient awake" phase. Circuitry 760 makes its correlation signal information 761 (determined during the "patient awake" phase) available to circuitry 770. In response to each breathing effort signal value that circuitry 750 now produces, circuitry 770 can access the correlation 761 it has received from (or has available to it in) circuitry 760 in order to identify the corresponding oral/nasal air pressure value for this patient. In other words, for any given value of breathing effort EP by sleeping patient 702, circuitry 770 can output a corresponding oral/nasal cavity air pressure PM (based on the correlation 761 established while the patient was awake). Air pressure in the patient's lungs (FIG. 8) is normally very similar to air pressure in the patient's oral/nasal cavity. Apnea due to an obstruction therefore has an effect on air pressure in the lungs very similar to the effect of breathing resistance 710 on air pressure throughout the respiratory system (i.e., the lungs and the oral/nasal cavity). Thus the oral/nasal cavity air pressure side of correlation 761 is a good indication of lung air pressure during an apneic event due to an obstruction in the patient's respiratory system. Accordingly, when an apneic event due to an obstruction occurs, breathing effort (output by circuitry 750) will increase, and circuitry 770 can use correlation 761 to find the corresponding previously determined value of oral/nasal cavity pressure, which (as the preceding sentences establish) can now be used as a measure of lung air pressure during the apneic event.

The air pressure value(s) that circuitry 770 thus determines from correlation 761 can be output by circuitry 770 to output circuitry 780. For example, circuitry 780 may be a display for displaying the air pressure value(s) output in human-readable form. Alternatively or in addition, circuitry 780 may be any suitable form of recording device (e.g., a printer, plotter, and/or memory) for making a more permanent record of the output value(s).

Recapitulating some aspects of the above, and also in some respects extending the above, in the procedure of this disclosure oral/nasal cavity pressure PM is used as a proxy measure of the pressure in the lung cavity. This is a reasonable assumption in view of the fluid dynamics of the respiratory system, i.e., because the pressure in the mouth and the lungs are on the same side of the obstruction 710 during the "patient awake" phase of the procedure. In that phase, most pressure loss due to the flowing fluid (air) is caused by restriction 710, and thus during expiration the lungs and mouth are both upstream from obstruction 710, while during inspiration the mouth and lungs are both downstream from obstruction 710.

During the procedure, the PPG signal is also acquired. The effort signal EP is determined from the PPG signal. This effort signal may be a relative measure of the degree of effort being applied by the patient during the respiration cycle. Circuitry 760 determines a functional relationship between EP and PM by varying breathing resistance using apparatus 710. This relationship is shown schematically in FIG. 10. This calibrates EP of the patient against a pressure (PM) indicative of the pressure in the lungs during respiration against a resistance.

Once calibrated, the patient can be monitored for respiratory effort during a sleep study using EP. When the patient becomes apneic due to a an obstruction (for example, occurring between the mouth and the lungs), the rise in pressure in the lungs can be determined from EP. When the patient suffers a central apnea, EP will drop to zero or a near zero value, thereby indicating this type of apnea.

Those skilled in the art will appreciate that the above-described procedure can be applied to any signal indicative of respiratory effort derived from a PPG or using alternative means such as piezo-bands, transthoracic impedance measurement, or the like.

Figure 11A:
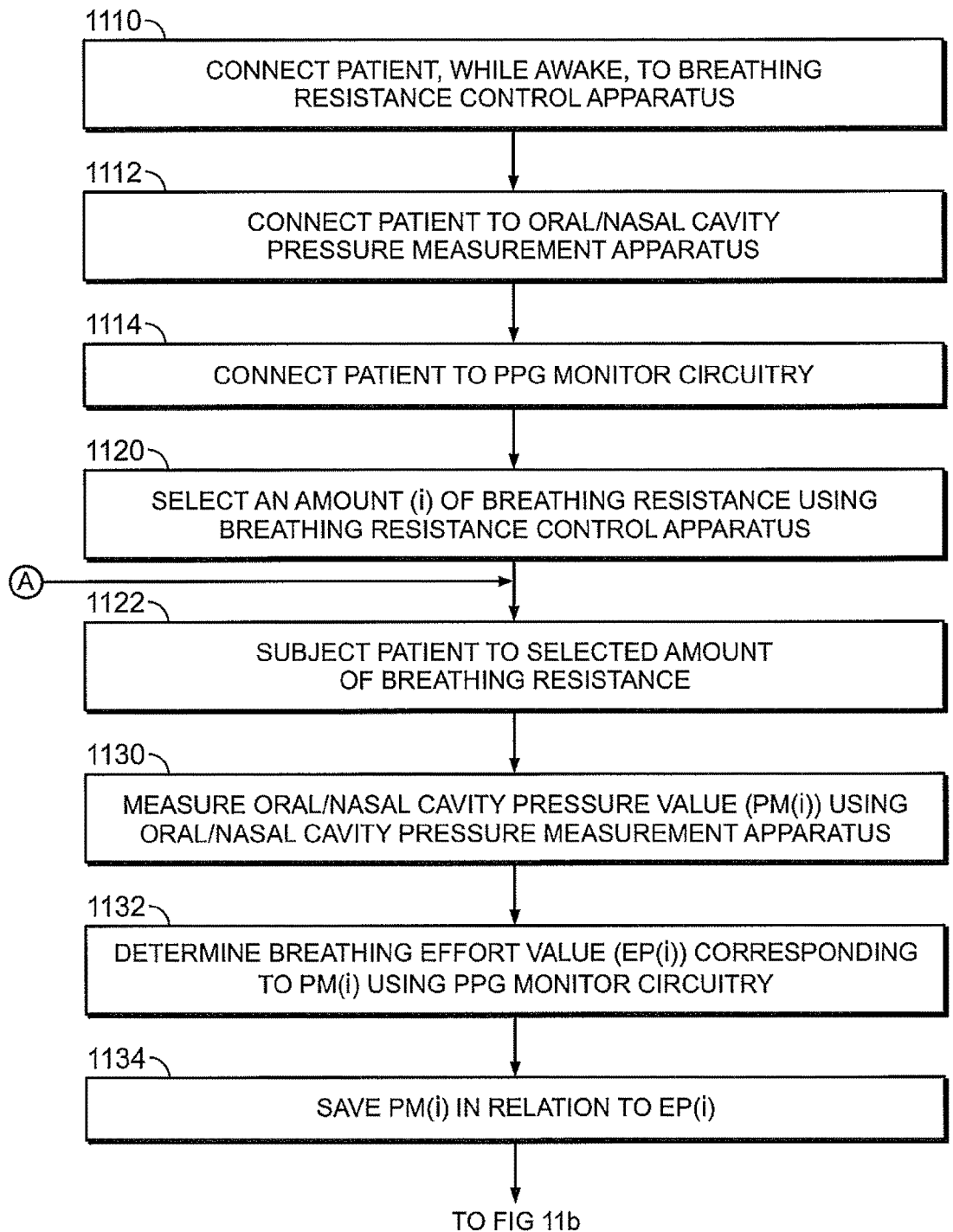
FIGS. 11a and 11b (which may be referred to collectively as FIG. 11) are collectively a simplified flow chart of an illustrative embodiment of methods in accordance with certain possible aspects of the disclosure.
Figure 11B:
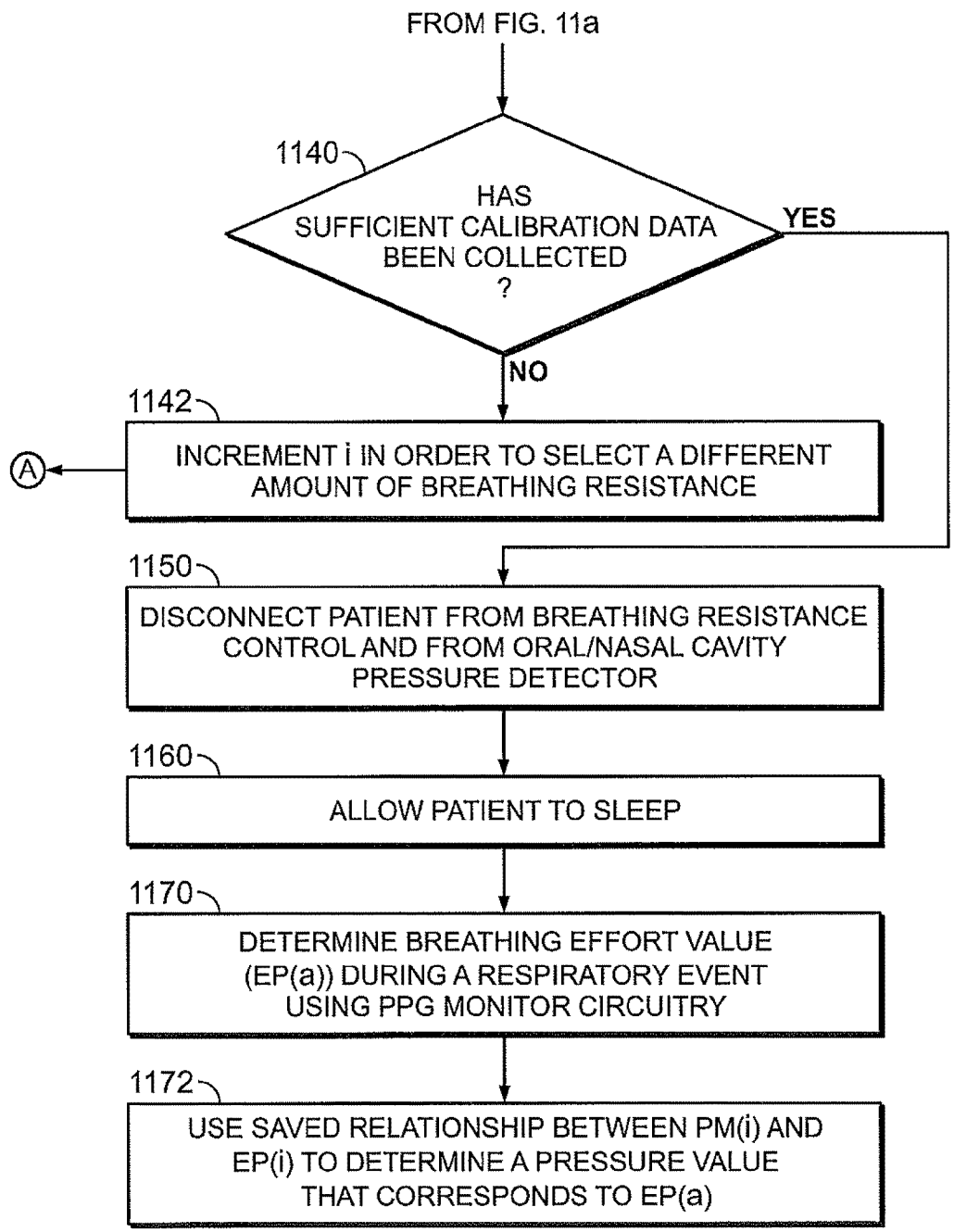

FIGS. 11*a* and 11*b* are collectively a flow chart for an illustrative embodiment of procedures or methods in accordance with the disclosure. For example, FIGS. 11*a* and 11*b* (which may be referred to collectively as FIG. 11) show an example of how apparatus 700 may be used in accordance with the disclosure. In such a case, steps 1110-1150 cover the "patient awake" phase of the procedure, while steps 1160-1172 cover the "patient asleep" phase of the procedure.

In step 1110, a patient (e.g., 702 in FIG. 7) who is awake is connected to breathing resistance control apparatus (e.g., 710 in FIG. 7). In step 1112, the patient is connected to oral/nasal cavity pressure measurement apparatus (e.g., 720 in FIG. 7). In step 1114, the patient is connected to PPG monitor circuitry (e.g., 730/740/750 in FIG. 7).

In step 1120 an amount of breathing resistance is selected. The letter i is used as an arbitrary index value for this selection. In step 1122 the patient is subjected to the selected amount of breathing resistance (e.g., using apparatus 710 in FIG. 7).

In step 1130, oral/nasal cavity air pressure is measured (e.g., using 720 in FIG. 7) while the patient is breathing against resistance i. This air pressure value is referred to as PM(i). In step 1132, the concurrent value of breathing effort (EP(i)) is measured (e.g., using 730/740/750 in FIG. 7).

In step 1134, PM(i) is saved in relation to EP(i) (e.g., in 760 in FIG. 7).

In step 1140, a test is performed to determine whether or not sufficient calibration data has been collected (e.g., to have a sufficiently complete and usable correlation of the type illustrated by 761 in FIG. 10). If the answer is no, then step 1142 is performed to increment i and select a different amount of breathing effort. Control then passes back to step 1122 for another iteration of that step and subsequent steps. On the other hand, if the answer to the test performed in step 1140 is yes, then control passes to step 1150.

In step 1150, the "patient awake" phase of the procedure concludes by disconnecting the patient from the breathing resistance control and from the oral/nasal cavity pressure detector. The "patient asleep" phase of the procedure can then begin with step 1160, in which the patient is allowed to sleep.

In step 1170, breathing effort (EP(a)) of the sleeping patient during a respiratory event (which can be an apneic event, hyponea, or increased effort due to compliance changes) is determined (e.g., using 730/740/750 in FIG. 7).

In step 1172, a pressure value corresponding to EP(a) is determined from the previously captured correlation between values of PM(i) and EP(i) (typically for several values of i). This determination of pressure corresponding to EP(a) may be made by 770 in FIG. 7 using correlation (e.g., 761) information from 760 in FIG. 7.

It will be understood that the foregoing method may be implemented using human-readable or machine-readable instructions on suitable systems or apparatus, such as those described herein.

Figure 12:
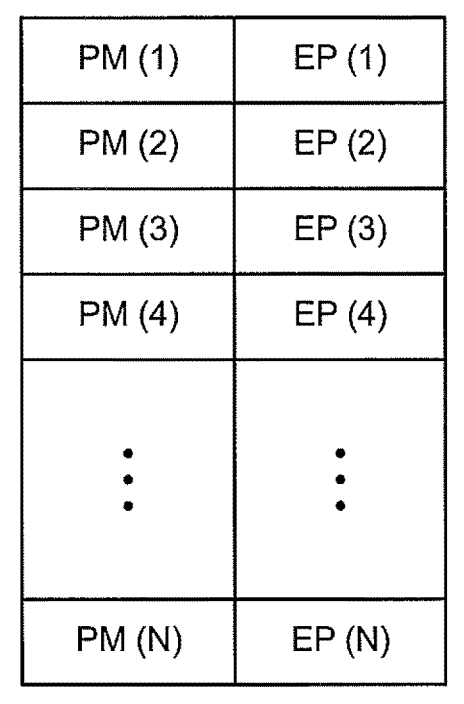

It will also be understood that the foregoing is only illustrative of the principles of the disclosure, and that various modifications can be made by those skilled in the art without departing from the scope and spirit of the disclosure. For example, if the correlation between EP and PM is represented by and/or stored as a curve such as 761 in FIG. 10, this curve may be the result of a conventional curve-fitting operation performed starting from several data points (each having an EP coordinate value and a PM coordinate value in the two-dimensional space shown in FIG. 10). Instead of or in addition to storing the curve that results from such curve-fitting, the curve may be abstracted as a mathematical function (e.g., PM=f(EP)) that is appropriate for approximating the curve. As still another example, the EP vs. PM data collected during the "patient awake" phase of the procedure may be stored in a data structure 1200 like that shown in FIG. 12. In such a data structure, concurrently occurring values of PM and EP are placed side by side and in order (for example, of increasing magnitude (i.e., PM(2) and EP(2) are respectively greater than PM(1) and EP(1); PM(3) and EP(3) are respectively greater than PM(2) and EP(2); and so on). After such a table has been constructed during the "patient awake" phase of the procedure, a value of EP that is collected during the "patient asleep" phase of the procedure can be converted to a corresponding value of PM by searching the table for the closest stored value of EP and then outputting the (horizontally) associated value of PM. Interpolation may be used to compute a PM value for a value of EP that is between two values of EP stored in table 1200. For example, if a value of EP is half-way between two stored values of EP, then the PM value output can be half-way between the two PM values stored in (horizontal) association with the above-mentioned two stored values of EP. If employed, features like the above-mentioned curve-fitting, mathematical function derivation, and/or data structure can be part of what circuitry 760 (FIG. 7) does and/or stores, as well as what circuitry 760 makes available to and/or transfers to circuitry 770. All of this data for various values of PM and EP is, of course, preferably in the form of electrical signals stored in and/or processed by various electrical circuit elements in accordance with the disclosure.

The following claims may also describe various aspects of this disclosure.

What is claimed is:
1. A method of calibrating respiratory effort of a patient for determining oral/nasal pressure, comprising:
using a pressure sensor when the patient is awake to measure air pressure in the patient's oral/nasal cavity during breathing with each of a plurality of successive different amounts of resistance to breathing to produce an oral/nasal pressure signal value for each respective amount of breathing resistance;

using respiratory effort monitoring apparatus when the patient is awake to acquire a respiratory effort signal from the patient during breathing with each of the plurality of successive amounts of resistance to breathing;

using respiratory effort signal processing circuitry to determine from the respiratory effort signal for each of the plurality of successive amounts of resistance to breathing a respective breathing effort signal value;

using storage circuitry to store a correlation between each oral/nasal pressure signal value and the breathing effort signal value concurrent with that respective oral/nasal pressure signal value, wherein the correlation is generated based on the plurality of successive amounts of resistance to breathing;

using the respiratory effort monitoring apparatus to acquire a respiratory effort signal from the patient while asleep;

using the respiratory effort signal processing circuitry to determine from the respiratory effort signal from the sleeping patient at least one breathing effort signal value for the sleeping patient;

using processing circuitry to determine a value indicative of the patient's oral/nasal pressure based on the stored correlation and the at least one breathing effort signal value determined for the sleeping patient; and outputting using a display the value indicative of oral/nasal pressure for the sleeping patient in human-readable form.

2. The method defined in claim 1 wherein the using respiratory effort signal processing circuitry comprises:
producing scalogram signals representing a scalogram of the respiratory effort signal;
analyzing the scalogram signals to identify breathing band signals in the scalogram signals; and
determining a breathing band amplitude signal value as an indication of breathing effort.

3. The method defined in claim 1 further comprising:
using a breathing resistance apparatus to subject the patient to the successive different amounts of resistance to breathing.

4. The method defined in claim 3 wherein the using the breathing resistance apparatus comprises:
applying the breathing resistance apparatus to the patient so that the patient can only breathe through an air flow passageway through the breathing resistance apparatus.

5. The method defined in claim 4 wherein the using the breathing resistance apparatus further comprises:
varying size of the air flow passageway through the breathing resistance apparatus to subject the patient to the successive different amounts of resistance to breathing.

6. The method defined in claim 1 wherein the using a pressure sensor comprises:
placing the pressure sensor in the patient's mouth.

7. The method defined in claim 1 wherein the using respiratory effort monitoring apparatus comprises:
using a photoplethysmograph ("PPG") monitoring apparatus.

* * * * *